US009968761B2

(12) United States Patent
Brecker

(10) Patent No.: US 9,968,761 B2
(45) Date of Patent: May 15, 2018

(54) PERCUTANEOUS GUIDEWIRE

(75) Inventor: Stephen Brecker, London (GB)

(73) Assignee: MEDTRONIC CV LUXEMBOURG S.A.R.L., Luxembourg (LU)

( * ) Notice: Subject to any disclaimer, the term of this patent is extended or adjusted under 35 U.S.C. 154(b) by 0 days. days.

(21) Appl. No.: 13/148,748

(22) PCT Filed: Feb. 12, 2010

(86) PCT No.: PCT/GB2010/000251
§ 371 (c)(1),
(2), (4) Date: Oct. 4, 2011

(87) PCT Pub. No.: WO2010/092347
PCT Pub. Date: Aug. 19, 2010

(65) Prior Publication Data
US 2012/0016342 A1    Jan. 19, 2012

(30) Foreign Application Priority Data
Feb. 12, 2009  (GB) .................................. 0902339.1

(51) Int. Cl.
*A61M 25/00*  (2006.01)
*A61B 5/00*  (2006.01)
*A61M 25/09*  (2006.01)

(52) U.S. Cl.
CPC ...... *A61M 25/09* (2013.01); *A61M 25/09025* (2013.01); *A61M 2025/0915* (2013.01); *A61M 2025/09083* (2013.01)

(58) Field of Classification Search
CPC ....................................................... A61B 5/00
USPC ......................................... 600/585, 587, 595
See application file for complete search history.

(56) References Cited

U.S. PATENT DOCUMENTS

| | | | |
|---|---|---|---|
| 4,538,622 A * | 9/1985 | Samson et al. ............... | 600/585 |
| 4,917,102 A | 4/1990 | Miller et al. | |
| 4,925,445 A * | 5/1990 | Sakamoto ............. | A61L 31/022 |
| | | | 600/585 |
| 5,040,543 A * | 8/1991 | Badera et al. ................ | 600/585 |
| 5,054,501 A * | 10/1991 | Chuttani et al. .............. | 600/585 |
| 5,129,890 A | 7/1992 | Bates et al. | |
| 5,143,085 A * | 9/1992 | Wilson .......................... | 600/585 |
| 5,221,269 A * | 6/1993 | Miller et al. .................. | 604/528 |
| 5,295,493 A * | 3/1994 | Radisch, Jr. .................. | 600/585 |

(Continued)

FOREIGN PATENT DOCUMENTS

EP    0 260 711 A2    3/1988
EP    0 769 306 A2    4/1997
(Continued)

OTHER PUBLICATIONS

International Search Report for PCT/GB2010/000251.
(Continued)

*Primary Examiner* — May Abouelela
(74) *Attorney, Agent, or Firm* — Medler Ferro Woodhouse & Mills PLLC

(57) ABSTRACT

A percutaneous guidewire comprising a distal end portion that is pre-formed in a curve that turns through more than 270 degrees. The stiffness of the guidewire may decrease continuously along the length of the curved distal end portion towards the tip of the guidewire and the radius of curvature of the curved distal end portion may also decrease towards the tip of the guidewire.

21 Claims, 9 Drawing Sheets

(56) References Cited

U.S. PATENT DOCUMENTS

| | | | |
|---|---|---|---|
| 5,358,479 A * | 10/1994 | Wilson | 604/95.04 |
| 5,365,943 A * | 11/1994 | Jansen | 600/585 |
| 5,372,144 A * | 12/1994 | Mortier et al. | 600/585 |
| 5,372,587 A * | 12/1994 | Hammerslag et al. | 604/95.04 |
| 5,722,425 A * | 3/1998 | Bostrom | 600/585 |
| 5,730,741 A * | 3/1998 | Horzewski et al. | 606/1 |
| 5,769,796 A * | 6/1998 | Palermo et al. | 600/585 |
| 5,846,210 A * | 12/1998 | Ogawa et al. | 600/585 |
| 5,881,732 A * | 3/1999 | Sung et al. | 128/898 |
| 5,882,346 A * | 3/1999 | Pomeranz et al. | 604/525 |
| 5,904,657 A * | 5/1999 | Unsworth et al. | 600/585 |
| 5,957,903 A * | 9/1999 | Mirzaee et al. | 604/524 |
| 6,004,279 A * | 12/1999 | Crowley et al. | 600/585 |
| 6,086,548 A * | 7/2000 | Chaisson et al. | 600/585 |
| 6,254,550 B1 * | 7/2001 | McNamara et al. | 600/585 |
| 6,308,090 B1 * | 10/2001 | Tu et al. | 600/374 |
| 6,428,489 B1 * | 8/2002 | Jacobsen et al. | 600/585 |
| 6,602,207 B1 * | 8/2003 | Mam et al. | 600/585 |
| 6,689,119 B1 * | 2/2004 | Di Caprio et al. | 604/523 |
| 6,716,183 B2 * | 4/2004 | Clayman et al. | 600/585 |
| 6,743,227 B2 * | 6/2004 | Seraj et al. | 606/41 |
| 6,884,225 B2 * | 4/2005 | Kato et al. | 600/585 |
| 7,081,114 B2 * | 7/2006 | Rashidi | 606/41 |
| 7,416,534 B2 * | 8/2008 | Nair et al. | 600/585 |
| 7,606,609 B2 * | 10/2009 | Muranushi et al. | 600/374 |
| 7,715,903 B2 * | 5/2010 | Hartley et al. | 600/433 |
| 7,824,345 B2 * | 11/2010 | Euteneuer et al. | 600/585 |
| 7,871,414 B2 * | 1/2011 | Hardin, Jr. | 606/108 |
| 7,963,947 B2 * | 6/2011 | Kurth et al. | 604/164.08 |
| 8,062,317 B2 * | 11/2011 | McGuckin et al. | 606/159 |
| 8,182,467 B2 * | 5/2012 | Nguyen et al. | 604/528 |
| 8,328,798 B2 * | 12/2012 | Witzel et al. | 606/41 |
| 8,401,673 B2 * | 3/2013 | Bowe et al. | 607/122 |
| 8,403,866 B2 * | 3/2013 | Seifert et al. | 600/585 |
| 8,409,114 B2 * | 4/2013 | Parins | 600/585 |
| 8,423,115 B2 * | 4/2013 | Koblish | 600/374 |
| 8,444,577 B2 * | 5/2013 | Bunch et al. | 600/585 |
| 8,500,697 B2 * | 8/2013 | Kurth et al. | 604/170.03 |
| 2002/0095102 A1 * | 7/2002 | Winters | 600/585 |
| 2003/0181828 A1 * | 9/2003 | Fujimoto et al. | 600/585 |
| 2003/0233058 A1 * | 12/2003 | Ewers et al. | 600/585 |
| 2004/0019359 A1 * | 1/2004 | Worley et al. | 606/129 |
| 2004/0039304 A1 * | 2/2004 | Connors et al. | 600/585 |
| 2004/0073141 A1 * | 4/2004 | Hartley et al. | 600/585 |
| 2004/0129352 A1 | 7/2004 | Shiota | |
| 2004/0147969 A1 * | 7/2004 | Mann et al. | 607/17 |
| 2004/0199087 A1 * | 10/2004 | Swain et al. | 600/585 |
| 2004/0199088 A1 * | 10/2004 | Bakos et al. | 600/585 |
| 2005/0240116 A1 * | 10/2005 | Saadat et al. | 600/549 |
| 2005/0271992 A1 * | 12/2005 | DeGrazia et al. | 431/215 |
| 2006/0116609 A1 * | 6/2006 | Kanuka | A61M 25/09 600/585 |
| 2006/0189896 A1 * | 8/2006 | Davis et al. | 600/585 |
| 2007/0032831 A1 | 2/2007 | Eigler et al. | |
| 2007/0162108 A1 * | 7/2007 | Carlson et al. | 623/1.34 |
| 2007/0225784 A1 | 9/2007 | Bly et al. | |
| 2008/0015471 A1 * | 1/2008 | Skujins et al. | 600/585 |
| 2008/0064988 A1 * | 3/2008 | Carter et al. | 600/585 |
| 2008/0077049 A1 * | 3/2008 | Hirshman | 600/585 |
| 2009/0105654 A1 | 4/2009 | Kurth et al. | |
| 2010/0030113 A1 * | 2/2010 | Morriss et al. | 600/585 |
| 2010/0030114 A1 * | 2/2010 | Nguyen et al. | 600/585 |
| 2010/0094310 A1 * | 4/2010 | Warring | A61M 25/0606 606/108 |
| 2010/0292566 A1 * | 11/2010 | Nagano et al. | 600/424 |
| 2012/0041422 A1 * | 2/2012 | Whiting et al. | 604/528 |
| 2012/0065481 A1 * | 3/2012 | Hunter et al. | 600/301 |
| 2013/0012834 A1 * | 1/2013 | Tamai et al. | 600/585 |

FOREIGN PATENT DOCUMENTS

| | | |
|---|---|---|
| EP | 0 778 043 A1 | 6/1997 |
| EP | 0 515 201 B1 | 9/1997 |
| EP | 1 105 181 B1 | 2/2004 |
| EP | 1 419 797 B1 | 6/2008 |
| JP | H07-255856 A | 10/1995 |
| WO | 99/03426 A1 | 1/1999 |
| WO | 00/32265 A1 | 6/2000 |
| WO | WO 00/32265 | 6/2000 |
| WO | 01/17601 A1 | 3/2001 |
| WO | 02/05886 A1 | 1/2002 |
| WO | 2004/018031 A2 | 3/2004 |
| WO | 2007/006055 A2 | 1/2007 |

OTHER PUBLICATIONS

Written Opinion of the International Searching Authority for PCT/GB2010/000251.

EP Patent No. 2 396 067 B1 (Appl. No. 10703669.1), Opposition by Alexander Zolyomi, Nov. 8, 2016.

EP Patent No. 2 396 067 B1 (Appl. No. 10703669.1), Opposition by Boston Scientific Scimed, Nov. 10, 2016.

EP Patent No. 2 396 067 B1 (Appl. No. 10703669.1), Reply by Medtronic CV Lyxembourg S.a.r.l., Apr. 20, 2017.

* cited by examiner

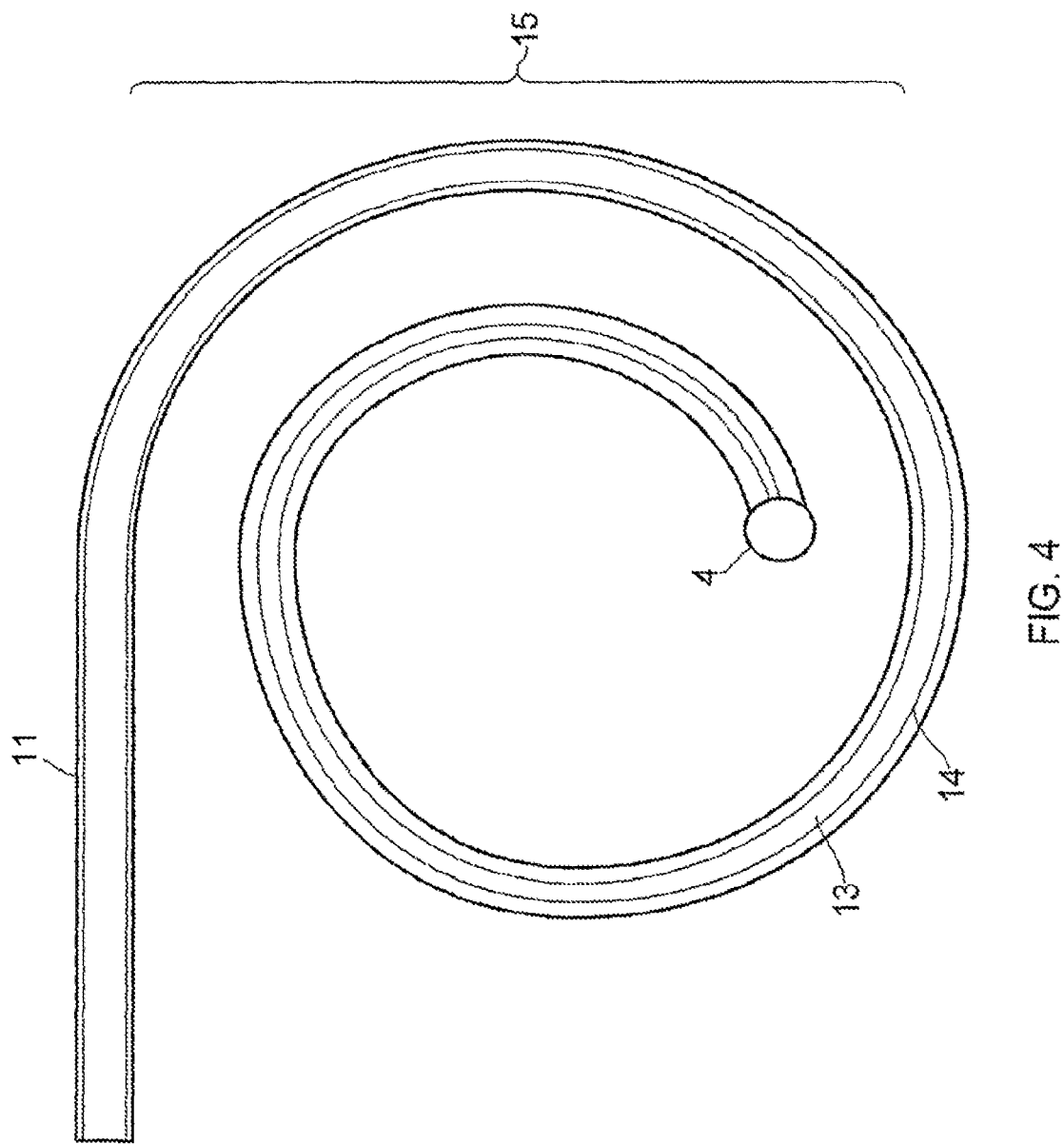

PERCUTANEOUS GUIDEWIRE

FIELD OF THE INVENTION

The present invention relates to percutaneous guidewires. Guidewires in accordance with embodiments of the present invention have particular, although not necessarily exclusive, application in the percutaneous delivery of replacement heart valves.

BACKGROUND

Percutaneous guidewires are commonly used in gastrointestinal, hepatobiliary and cardiac procedures. They are introduced percutaneously and manipulated through a vessel to the site of interest, using fluoroscopy, for example, to monitor the path taken by the guidewire. They are usually the first medical device that will reach the site of interest. Once in place, they can subsequently be used to reliably guide catheters, endoscopes and other delivery systems to the site of interest, by passing these delivery systems over the guidewire.

The environments in which percutaneous guidewires must operate tend to place conflicting constraints on their design. For instance, the guidewire must typically have sufficient stiffness to enable a physician to pass them along the vessel they are introduced through, as well as to accurately guide the delivery systems that they are subsequently employed to deliver. On the other hand, they need to be flexible enough to follow the sometimes tortuous paths they must follow through the vasculature to reach the site of interest. An overly stiff guidewire also increases the risk of the tip of the guidewire puncturing the wall a vessel wall or other tissue it encounters.

Most modern guidewires have a composite construction consisting of a solid metal core (1) and outer metal coil (3) terminating at a rounded, atraumatic tip (4), as illustrated schematically in FIG. 1. At a distal end portion (2) of the guidewire, the inner core tends to be ground or drawn so that its diameter reduces towards to the tip of the guidewire. This reduces the stiffness of the distal end portion of the guidewire to reduce the risk of the wire end puncturing soft tissue.

A majority of guidewires are supplied straight, although many are provided with a tip portion that can be manually bent into a desired shape by the user, for example to aid in navigating a tortuous path. In some case the user may bend the end of the wire to help minimise the likelihood that the wire end causes trauma if it impinges on soft tissue; on impact, force is transmitted radially rather than longitudinally along the wire.

More recently, it has been proposed to manufacture guidewires with a pre-formed curve at their distal end portion (2), as seen schematically in FIGS. 2a and 2b. The curved form of the end of these so called 'J-tip' guidewires further reduces the likelihood of trauma if the end of the wire impacts soft tissue as it is being advanced.

One area of increasing importance for the use of guidewires is in coronary interventions and, more recently, structural interventions of the heart, in particular percutaneous heart valve (PHV) placement. When implanting a PHV at the aortic position a guidewire (5) is first fed into the left ventricle (7) of the heart (6), as illustrated in FIG. 3. This wire in then used to guide the PHV into position, typically involving iterative pushing and pulling of the guide wire before the artificial valve is seated in the correct position.

The demands placed on a guidewire by this particular application are great and are at (or in some cases beyond) the limit of current devices.

More specifically, in order to successfully place the artificial valve the wire must be stiff enough at the aortic valve to sufficiently support the delivery system. However, the tip must be atraumatic enough to prevent damaging the thin ventricular wall should it come into contact during the pushing and pulling of the valve delivery.

Typically a straight guidewire is used for this. The guide wire may, however, have a user imparted bend to help it conform to the V shape of the ventricle (as shown in FIG. 3a). Even then there is still a high risk, especially if the user has imparted a bend to the wire with a small radius of curvature, that if the wire contacts the ventricular wall it will kink and potentially cause traumatic injury (see FIG. 3b).

SUMMARY OF INVENTION

It is a general, preferred aim of the present invention to provide percutaneous, atraumatic guidewires that have a lower propensity to puncture soft tissue than known guidewires. Such guidewires may be useful, for instance, for PHV placement and other procedures in which the distal end of the guidewire might inadvertently contact a very thin tissue wall, such as the ventricular wall.

The present invention provides a percutaneous guidewire comprising a distal end portion that is pre-formed in a curve that turns through more than 270 degrees. Preferably the curve turns through at least one complete revolution, i.e. at least 360 degrees.

The long curve helps to prevent any part of the wire causing trauma to soft tissues as very little force can be longitudinally transmitted to the tip. The looping curve also provides for a longer transition between the stiff support section of the wire and soft atraumatic tip in the case where the stiffness of the wire decreases towards the tip, as is preferred.

The distal end portion of the guidewire may be resiliently deformable so that if it is deformed either during delivery or in use, it resumes its pre-formed curved shape once the external force is removed. That is to say, the pre-formed curvature is that shape that the wire adopts in a relaxed state.

Preferably the stiffness of the guidewire decreases along the length of the curved distal end portion towards the tip of the guidewire. The transition from the stiffer, straight proximal portion of the guidewire towards the tip at the distal end is preferably a smooth transition with no steps, providing a continuous decrease in stiffness along the distal end portion of the wire towards its tip. To minimise the propensity of the wire to kink at the start of the curved portion, the wire is preferably configured so that the stiffness starts to decrease in the straight portion of the wire and then continues to decrease along the length of the curved portion. The rate at which the stiffness of the guidewire decreases along the length of the curve may be linear. Alternatively it may be proportional to the (preferably decreasing) radius of curvature.

Particularly in the case where the guidewire is of a composite structure, having an internal core wire and an outer spiral wrapping, the change in stiffness can be achieved through a reduction in the diameter of the wire core towards the tip. The tapering of the wire may start on the straight portion of the wire (preferably close to but not at the start of the curved portion) and continue over the transition from the straight portion of the wire to the curved portion, and along the length of the curved portion to the tip. The outer spiral winding may be of constant diameter.

The radius of curvature of the curved distal end portion may decrease towards the tip of the guidewire. In this case, the rate of change of the radius of curvature is typically non-linear, with the rate of change decreasing towards the tip. This allows for multiple loops within one another, making it even less likely that the tip of the wire can cause trauma, whilst minimising the space occupied by the end portion of the guidewire. The curvature of the distal end portion may, for example, be a logarithmic spiral or, starting from the tip, the radius of curvature of the distal end portion may increase for every 90 degrees of curvature according to a Fibonacci sequence. Other non-linear changes in radius are also possible.

Particularly in the case where the guidewire is intended for use in placement of a PHV, the maximum radius of the curved distal end portion is preferably 3.5 cm or less.

BRIEF DESCRIPTION OF THE DRAWINGS

Embodiments of the invention will now be described, by way of example only, with reference to the accompanying drawings, in which;

FIG. 4 shows a side elevation of a guide wire in accordance with an embodiment of the invention;

DESCRIPTION OF EMBODIMENTS

Figure 1:
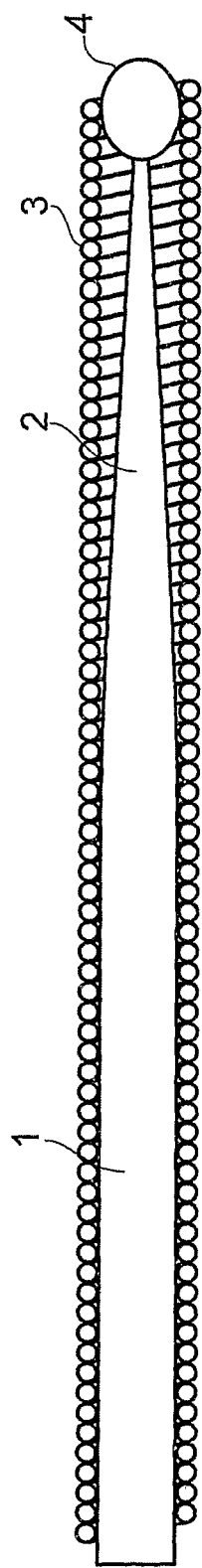
FIG. 1 shows a side elevation of a prior art guide wire.
Figure 2A:
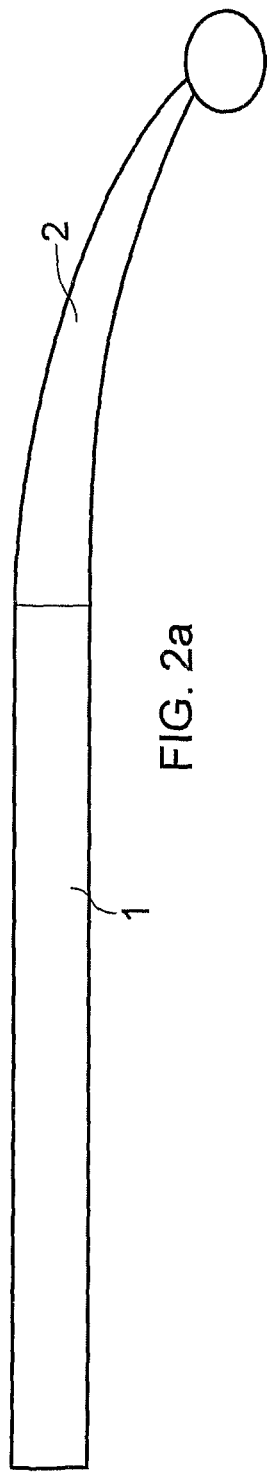
FIG. 2a shows a side elevation of another prior art guide wire.
Figure 2B:
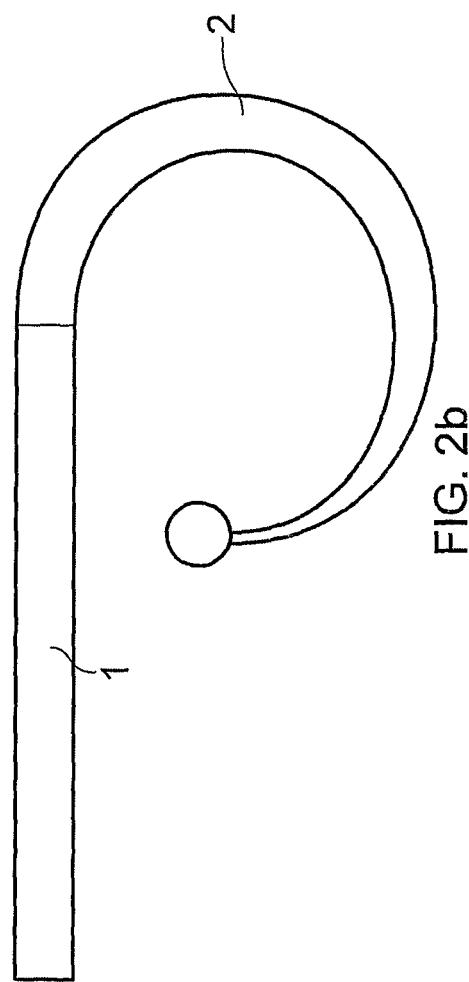
FIG. 2b shows a side elevation of another prior art guide wire.
Figure 3A:
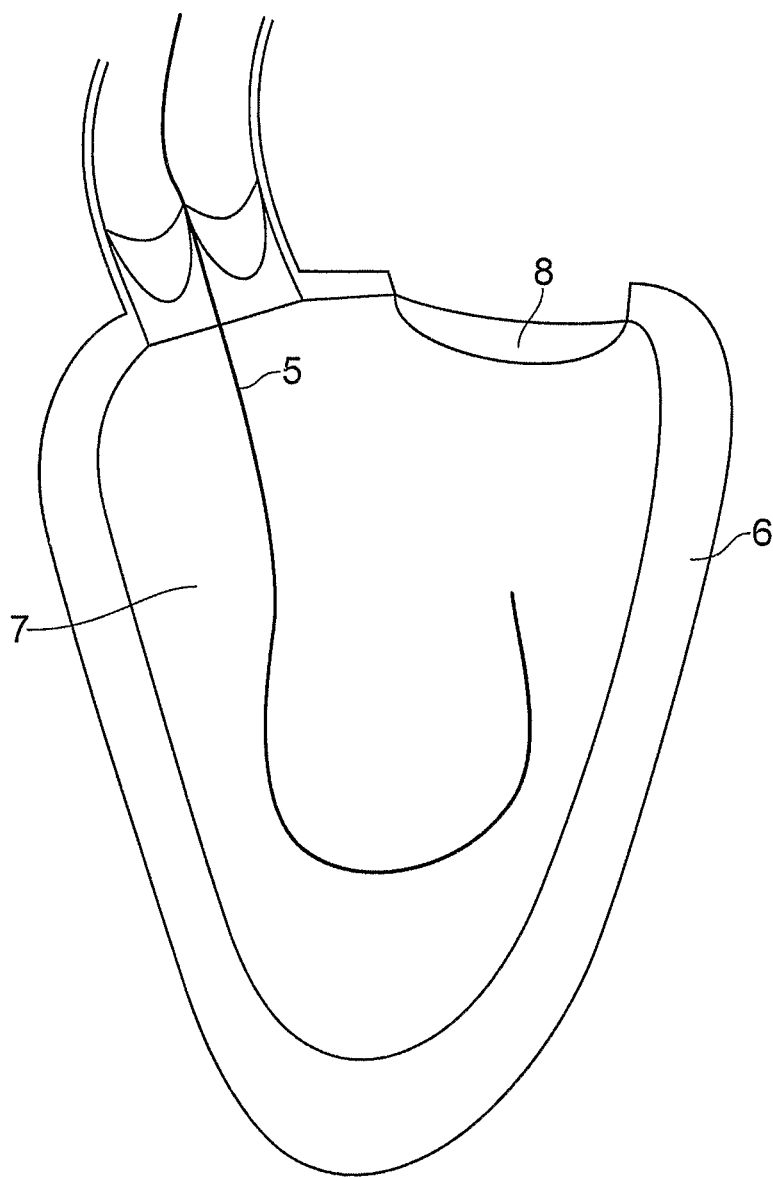
FIG. 3a shows a guide wire in situ in a patient's heart.
Figure 3B:
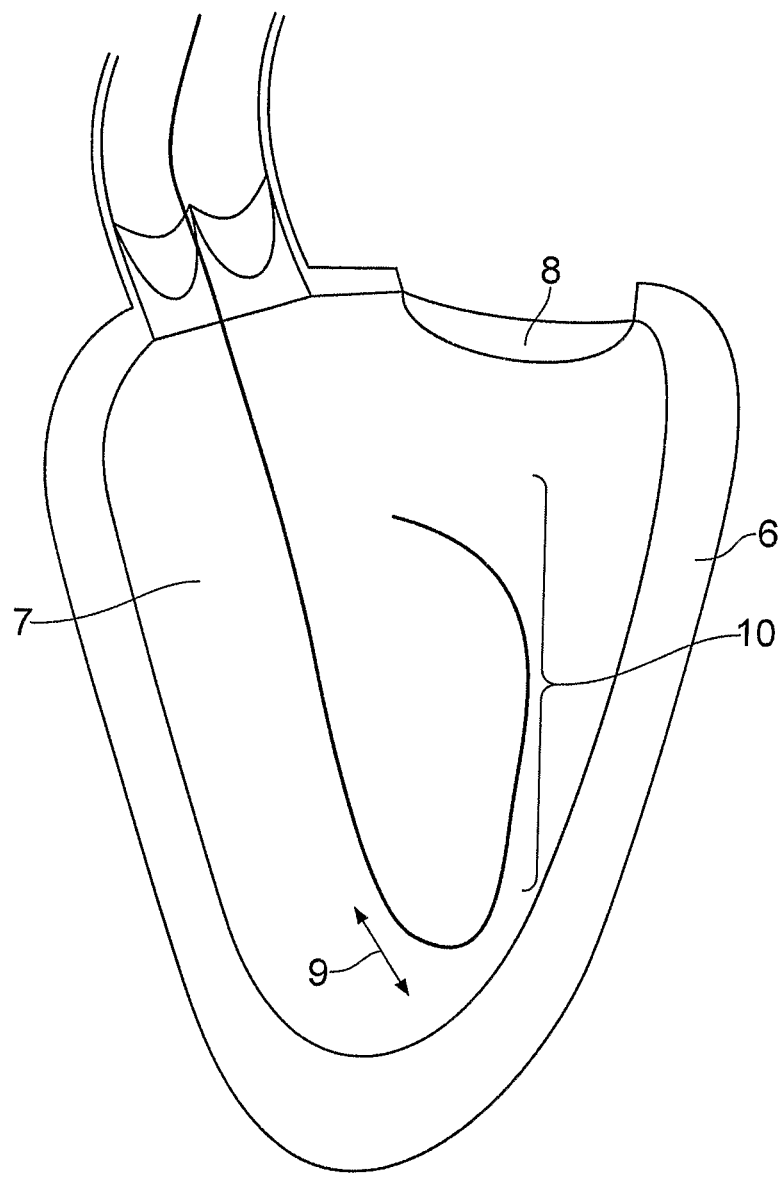
FIG. 3b shows the guide wire of FIG. 3a after contact with the ventricular wall.

The various embodiments of the invention described below provide atraumatic guidewires that are particularly suitable for use in percutaneous heart valve (PHV) delivery. The guidewires have resiliently deformable distal end portions that are pre-formed, e.g. during manufacture, to have a curved geometry that is designed to minimise the risk of trauma in the event that the tip portion contacts the ventricular wall as the PHV is being manipulated into position using the guidewire.

FIG. 4 shows a guidewire in accordance with one embodiment of the invention. The guidewire comprises a solid metal core wire (13) that is surrounded by an outer casing (14). The outer casing may, for example, be a spirally wound metal casing, as in known composite guidewires. The tip of the guide wire is also fitted with a bulbous atraumatic tip (4).

The core and casing of the guidewire may be constructed from materials that are conventionally used for percutaneous guidewires, including, for example, stainless steel and/or metal alloys such as nitinol (a nickel-titanium alloy).

In an alternative embodiment of the invention, the outer casing may be formed as a polymer coating. The outer surface of the coating is preferably formed of a hydrophilic material. Known hydrophilic polymers may be used, either to form the complete polymer coating or as a surface coating on another polymer that forms the main outer casing. Where a hydrophilic coating is used, it is preferred to leave a 'handle portion' of the guidewire (i.e. at portion at the proximal end of the wire that is grasped by the physician) free of the coating. For instance, the coating may be applied only to the distal ⅔ or less or even to the distal ⅓ or less of the guidewire.

This helps to ensure that the physician can maintain a good grip on the guidewire even when wearing wet gloves.

A main portion (11) of the guidewire is straight but, in accordance with present invention, a distal end portion (15) of the guidewire is pre-formed in a curve, which in this example turns through about 540 degrees. In this way the tip (4) of the guidewire sits within the looped end portion (15) significantly reducing the likelihood that it will make contact with the ventricular wall. Rather, in the event that the end portion of the guidewire is thrust into contact with the ventricular wall, it will most likely be a relatively gently curved part of the guidewire that makes contact and resiliently deforms greatly reducing the chances of any trauma.

In the illustrated example, the core wire (13) tapers gradually along the length of the curved end portion (15) from the transition between straight and curved portions to the tip of the guidewire. In an alternative embodiment, the taper may commence proximally of the transition between straight and curved portions (e.g. at or near the point labelled 'A' in FIG. 5). In this way, as the taper commences on the straight portion, rather than at the transition, if there is a step at the outset of the taper, this step will not be at the start of the curvature (the most likely place for a kink to form).

The reduction in diameter of the core wire means that the stiffness of the core, and hence the overall guidewire, decreases towards the tip. This decreased stiffness makes the wire less traumatic, compensating at least to some degree (and preferably substantially entirely) for the greater trauma that might otherwise result from the parts of the guidewire end portion having a smaller radius of curvature.

Figure 5:
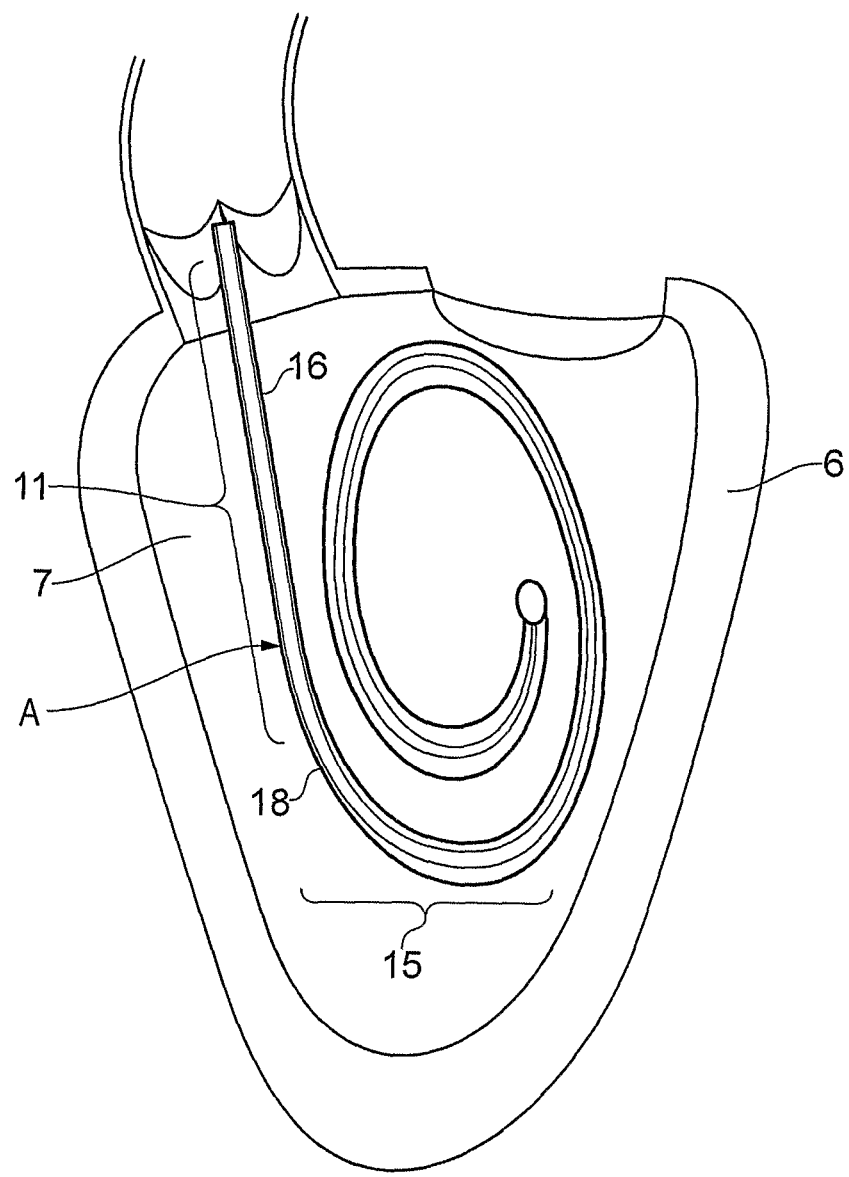
FIG. 5 shows the guide wire of FIG. 4 in situ in the left ventricle of a patient's heart.

Overall, the curvature of the guidewire allows a much more gradual transition from a stiff core section to a flexible core section than would be possible with a straight configuration, given the space constraints of the left ventricle, as best seen in FIG. 5, which shows the guidewire of FIG. 4 after it has been introduced into the left ventricle (7) of the patient's heart (6).

It can be seen that there is a potential kink point (18) at the point where the straight part (11) of the guide wire meets the curved end portion (15), as there is a step change in the radius of curvature of the guidewire at this transition between the straight portion (11) and the curved section (15). A kink s undesirable as this would create a sharp bend that might subsequently result in atraumatic contact with the ventricular wall.

Figure 6:
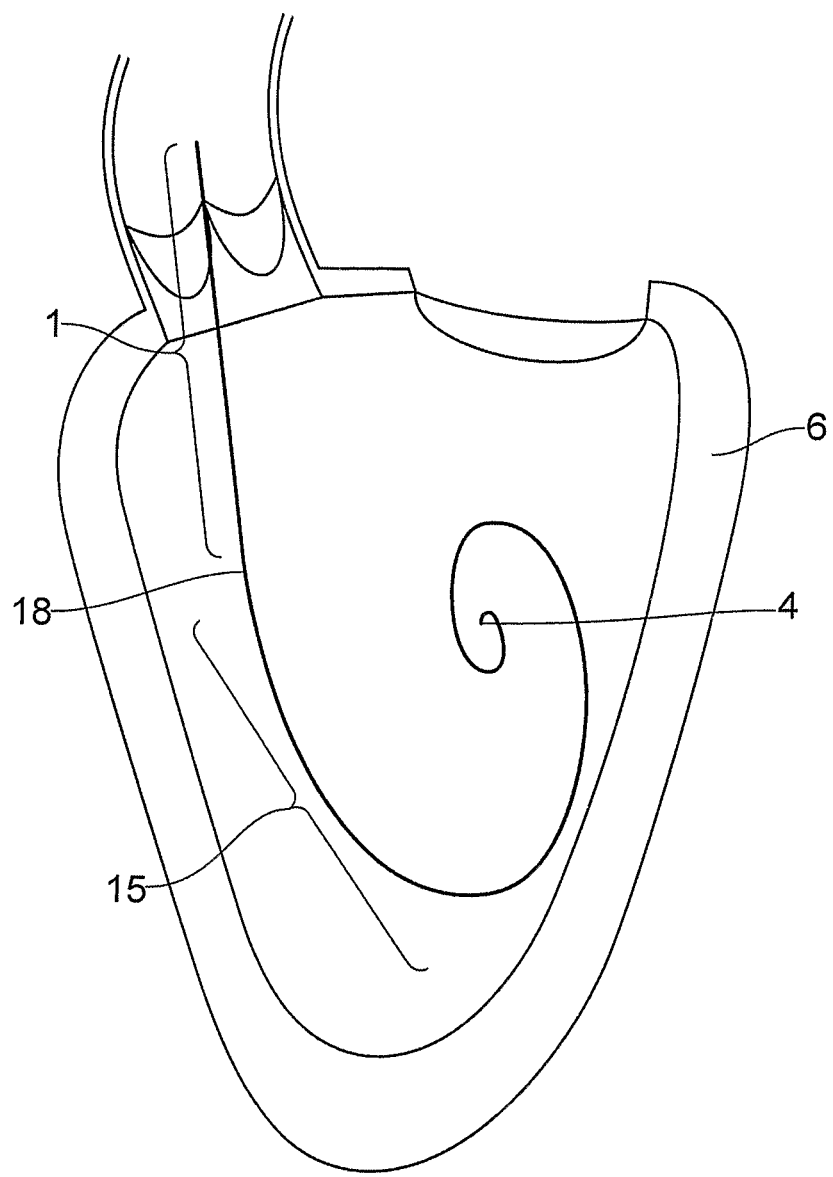
FIG. 6 shows a guidewire in accordance with a further embodiment of the invention in situ in a patient's heart.

To minimise the propensity of the guidewire to kink at this point, the transition between the straight portion (11) of the guidewire and the curved end portion (15) is preferably gradual and has no steps, as seen for example in FIG. 6.

More specifically, looking at FIG. 6, which shows the guidewire in situ in the heart (6), to achieve a gradual transition the radius of curvature at the transition is relatively large. It would be undesirable however, and in fact impractical, to maintain such a large radius of curvature along the length of the curved end portion because the overall effective area of this portion would become too large to be accommodated in the ventricle; typically the maximum diameter of the curved portion should be no more than 3.5 cm. To cater for patients with a smaller than average ventricle, a maximum diameter of 2.5 cm may be desirable. Generally, however, to avoid to tight a spiral, that might lead to trauma, the maximum diameter is at least 1 cm.

Preferably, therefore, as in the illustrated examples, the radius of curvature decreases significantly towards the tip of the guidewire, so that the curved portion spirals inwardly. In this particular example, the radius of the curved portion (15) increases, as one moves away from the tip (4), with a logarithmic spiral. This means that at the transition point (18) between the straight portion of the guide wire (11) and the curved section (15), there is not a sharp transition and therefore the likelihood of a kink at this point (18) is lowered.

Figure 7A:
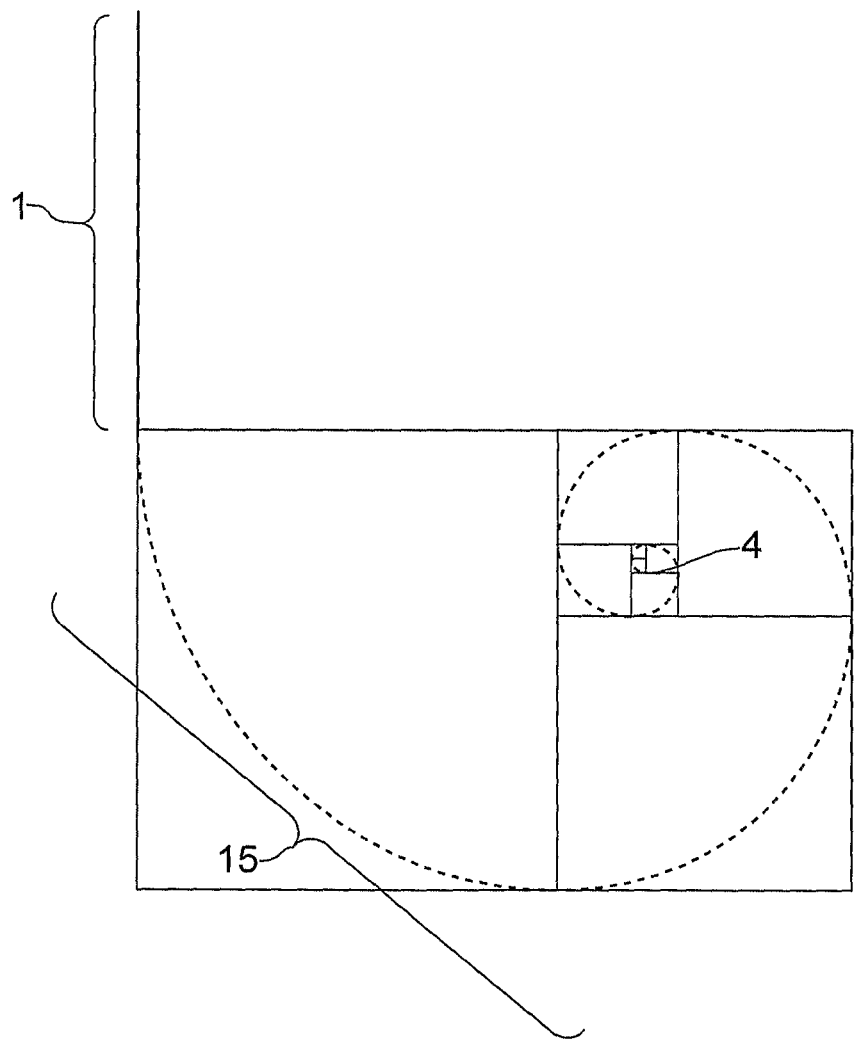
FIG. 7a schematically shows the geometry of a guidewire in accordance with an embodiment of the invention, in which the radius of curvature increases from the tip in accordance with a Fibonacci sequence.
Figure 7B:
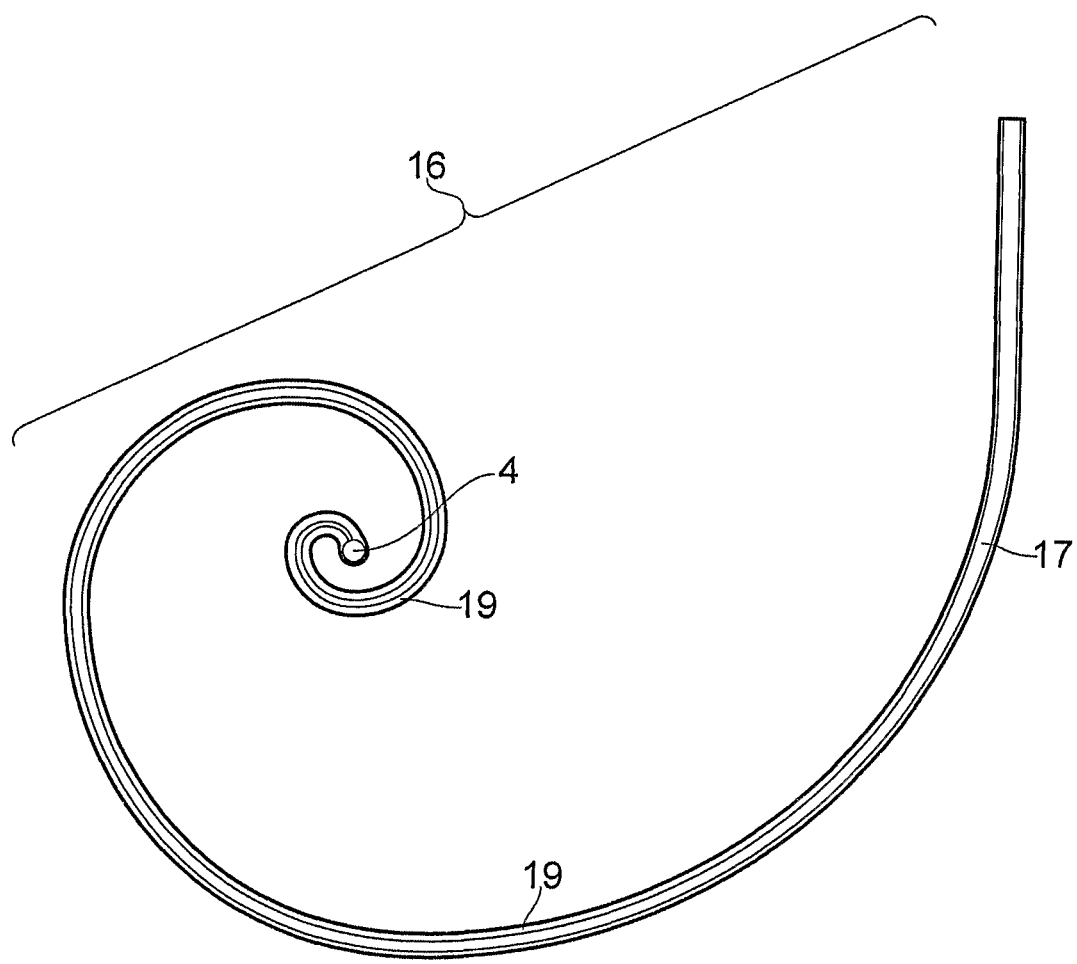
FIG. 7b shows a side elevation of a guidewire having a geometry as in FIG. 7a in accordance with an embodiment of the invention.

FIGS. 7a and 7b illustrate another embodiment of the invention, wherein the radius of the curved section (15) increases, as one moves away from the tip (4). In this embodiment the relationship between successive radii after each 90 degree rotation approximates a Fibonacci sequence (Fn=Fn-1+Fn-2: e.g. 1 mm, 1 mm, 2 mm, 3 mm, 5 mm, 8 mm, 13 mm, 21 mm), in order to further smooth the transition (18) between the straight portion of the guide wire (11) and the curved section (15), whilst minimising the effective area occupied by the curved portion of the guidewire.

In this example, as seen in FIG. 7b, core (17) of the guide wire (16) is formed from a metal wire, the diameter of which tapers towards a point at the bulbous atraumatic tip (4). The core wire (17) is coated in a flexible polymer (19) that is itself hydrophilic or has a hydrophilic coating.

Figure 8:
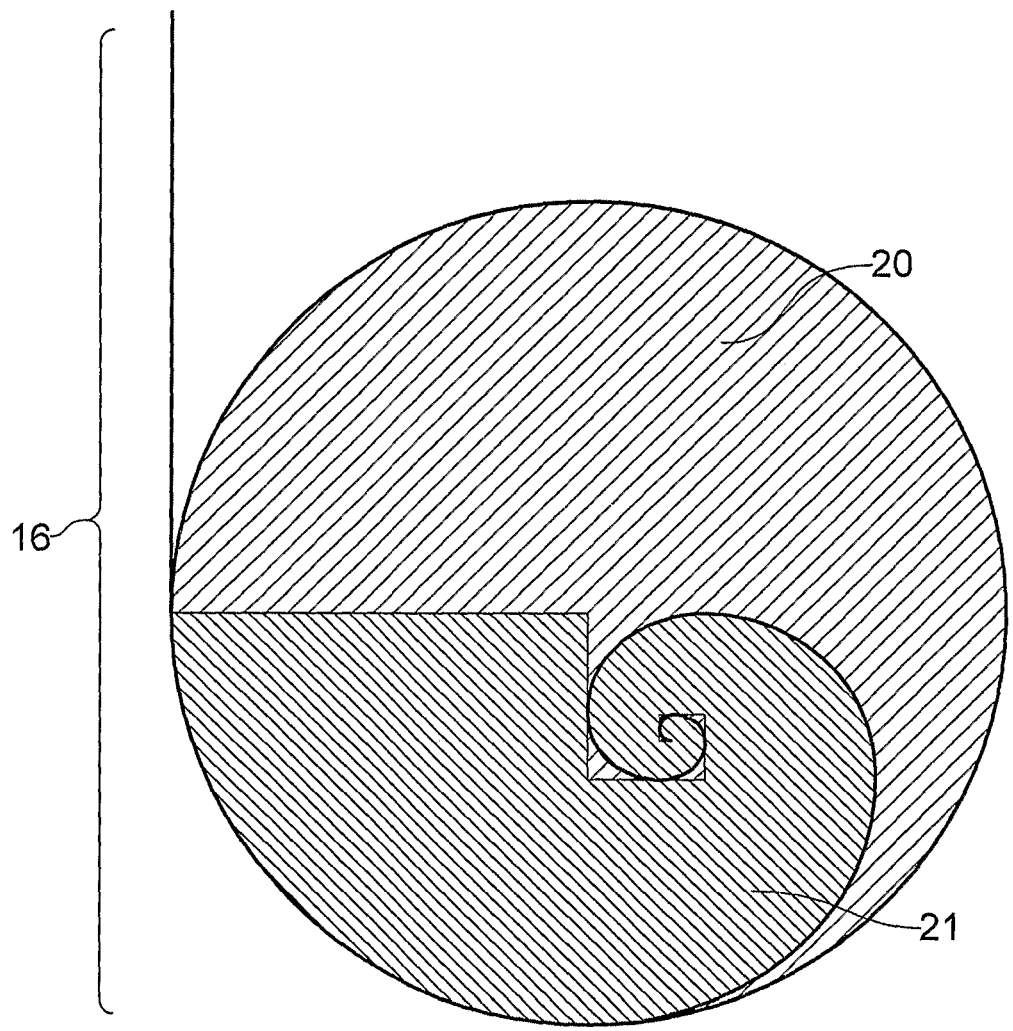
FIG. 8 shows the effective area of an embodiment of the invention having a decreasing radius of curvature towards the tip of the guidewire in comparison with effective area that would be occupied by a circular loop.

FIG. 8 shows a comparison of the effective area of a circular loop (20), and the reduced area (21) occupied by a Fibonacci spiral in a guide wire (16) as shown in FIGS. 7a and 7b. It can be seen that the Fibonacci spiral occupies an area that is reduced by about 2.4 times compared with the circular loop.

While the invention has been described in conjunction with the exemplary embodiments above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

The invention claimed is:

1. A percutaneous guidewire comprising: a solid metal core wire; and
   an outer casing surrounding the solid metal core wire, wherein the solid metal core wire includes a straight portion and a distal end portion that is pre-formed in a curve that turns through more than 360 degrees, the pre-formed curve being substantially in a single plane, wherein the straight portion and the distal end portion are a single wire,
   wherein a stiffness of the solid metal core wire continuously decreases from a point on the straight portion along an entire length of the curved distal end portion towards a tip of the solid metal core wire, wherein the point on the straight portion is proximal of a transition of the solid metal core wire from the straight portion to the curve in the distal end portion, and
   wherein a maximum diameter of the pre-formed curve of the curved distal end portion is at least 1 cm and no more than 3.5 cm.

2. A guidewire according to claim 1, wherein the pre-formed curve turns through at least 540 degrees.

3. A guidewire according to claim 1, wherein the distal end portion of the solid metal core wire is resiliently deformable.

4. A guidewire according to claim 1, wherein a rate at which the stiffness of the solid metal core wire decreases along the length of the curve is proportional to a radius of curvature of the curved distal end portion.

5. A guidewire according to claim 1, wherein a rate of change of the stiffness of the solid metal core wire along the length of the curve is linear.

6. A guidewire according to claim 1, wherein the decrease in stiffness results from a reduction in a diameter of the solid metal core wire.

7. A guidewire according claim 1, wherein a radius of curvature of the curved distal end portion decreases towards the tip of the solid metal core wire.

8. A guidewire according to claim 7, wherein a rate of change of the radius of curvature is non-linear.

9. A guidewire according to claim 8, wherein the rate of change of the radius of curvature decreases towards the tip of the solid metal core wire.

10. A guidewire according to claim 9, wherein the radius of curvature of the distal end portion is a logarithmic spiral.

11. A guidewire according claim 1, wherein the maximum diameter of the pre-formed curve of the curved distal end portion is at least 1 cm and no more than 2.5 cm.

12. A guidewire according to claim 1, wherein the outer casing is a metal coil.

13. A guidewire according to claim 1, wherein the outer casing is a polymeric coating.

14. A guidewire according to claim 13, wherein at least a portion of an outer surface of the polymeric coating is hydrophilic.

15. A guidewire according to claim 14, wherein a proximal end portion of the solid metal core wire does not include a hydrophilic coating.

16. A guidewire according to claim 1, further comprising a rounded atraumatic tip.

17. A percutaneous guidewire comprising:
    a solid metal core wire including,
    a straight portion, and
    a distal end portion that is continuous with the straight portion, wherein the distal end portion is pre-formed in a curve that turns through more than 360 degrees, the pre-formed curve being substantially in a single plane, and
    an outer jacket surrounding the solid metal core wire, wherein a stiffness of the solid metal core wire continuously decreases along an entire length of the curved distal end portion towards a tip of the guidewire,
    wherein a diameter of the solid metal core wire tapers along the length of the curved distal end portion,
    wherein the taper begins proximal of a transition from the straight portion to the curve of the distal end portion, and wherein a maximum diameter of the pre-formed curve of the curved distal end portion is at least 1 cm and no more than 3.5 cm.

18. A guidewire according to claim 17, wherein a rate at which the stiffness of the solid metal core wire decreases along the length of the curve is proportional to a radius of curvature of the curved distal end.

19. A guidewire according to claim 17, wherein a rate of change of the stiffness of the solid metal core wire along the length of the curve is linear.

20. A guidewire according claim 17, wherein a radius of curvature of the curved distal end portion decreases at a non-linear rate towards a tip of the solid metal core wire.

21. A guidewire according to claim 20, wherein the radius of curvature of the distal end portion is a logarithmic spiral.

* * * * *